United States Patent [19]
Koulu et al.

[11] Patent Number: 6,046,317
[45] Date of Patent: Apr. 4, 2000

[54] DNA MOLECULE ENCODING A MUTANT PREPRO-NEUROPEPTIDE Y, A MUTANT SIGNAL PEPTIDE, AND USES THEREOF

[75] Inventors: Markku Koulu, Piispanristi; Matti Karvonen; Ullamari Pesonen, both of Turku; Matti Uusitupa, Kuopio, all of Finland

[73] Assignee: Hormos Medical Oy, Ltd., Finland

[21] Appl. No.: 08/994,946

[22] Filed: Dec. 19, 1997

[51] Int. Cl.[7] .......................... C07H 21/04; C12N 15/00; C12N 15/63; C12N 15/85
[52] U.S. Cl. .......................... 536/23.5; 435/6; 435/252.3; 435/320.1; 435/325; 435/455; 536/23.1
[58] Field of Search .......................... 435/6, 252.3, 320.1, 435/325, 455; 536/23.1, 23.5

[56] References Cited

U.S. PATENT DOCUMENTS 5,455,164  10/1995  Turner .......................................... 435/6

FOREIGN PATENT DOCUMENTS 9527782  10/1995  WIPO .
9850563  11/1998  WIPO .

OTHER PUBLICATIONS

Minth et al. Cloning, characterization, and DNA sequence of a human cDNA encoding neuropeptide tyrosine. Proc. Natl. Acad. Sci. USA 81:4577–4581, Jul. 1984.

Erickson et al. Attenuation of the obesity syndrome of ob/ob mice by the loss of neuropeptide Y. Science 274:1704–1707, Dec. 1996.

Jaenisch, R. Transgenic animals. Science 240: 1468–1474 Jun. 1988.

Larhammar et al. Structure and expression of the rat neuropeptide Y gene. Proc. Natl. Acad. Sci. USA 84: 2068–2072, Apr. 1987.

Uusitupa, M.I.J. et al. (1988). "Neuropeptide Y: a novel link between the neuroendocrine system and cholesterol metabolism." *Ann. Med.* 30:508–510.

Karvonen, M.K. et al. (1988). "Association of a leucine(7)–to–proline(7) polymorphism in the signal peptide of neuropeptide Y with hihg serum cholesterol and LDL cholesterol levels." *Nature Genetics* 4:1434–1437.

Roche, C. et al. (1997). "Genetic studies of neuropeptide Y and neuropeptide Y receptors Y1 and Y5 regions in morbid obesity." *Diabetologia* 40:671–675.

Thorsell, A. et al. (1996). "Cationic lipid–mediated delivery and expression of prepro–neuropeptide Y cDNA after intraventricular administration in rat: feasibility and limitations." *Regulatory Peptides* 61:205–211.

Nystrom, F. et al. (1996). "A Population Study of Plasma Neuropeptide Y: Correlations with Components of the Metabolic Syndrome." *Blood Pressure* 5:349–353.

*Primary Examiner*—Bruce R. Campell
*Assistant Examiner*—Anne-Marie Baker
*Attorney, Agent, or Firm*—Rothwell, Figg, Ernst & Kurz, P.C.

[57] ABSTRACT

The invention relates to a DNA sequence comprising a nucleotide sequence encoding a prepro-neuropeptide Y (PreproNPY) where the leucine amino acid in position 7 of the signal peptide part of said preproNPY has been replaced by proline. The invention concerns further the mutant signal peptide as such or associated with any other cleavage product of preproNPY, methods for the determination, in a biological sample, of said DNA sequence or said peptide. Furthermore, this invention relates to a method for diagnosing a predisposition for increased serum cholesterol or LDL cholesterol level in a human subject, and to methods for treating a human subject diagnosed for predisposition for increased serum cholesterol or LDL cholesterol. Transgenic animals carrying either the mutant sequence or the normal sequence are also within the scope of this invention.

7 Claims, 5 Drawing Sheets

HUMAN NEUROPEPTIDE Y (NPY) GENE

SEQ ID NO:1 (M14295)

```
1   ccgcttcttc aggcagtgcc tggggcggga gggttggggt gtgggtggct ccctaagtcg
61  acactcgtgc ggctgcggtt ccagcccccct cccccgcca ctcaggggcg ggaagtggcg
121 ggtgggagtc acccaagcgt gactgcccga ggcccctcct gccgcggcga ggaagctcca
181 taaaagccct gtcgcgaccc gctctctgcA CCCCATCCGC TGGCTCTCAC CCCTCGGAGA
241 CGCTCGCCCG ACAGCATAGT ACTTGCCGCC CAGCCACGCC CGCGCGCCAG CCACCGTGAG
301 tgctacgacc cgtctgtcta ggggt
```

SEQ ID NO:2 (M14296)

```
                                                                    C
                                                                    ↓
1   cccgtccgtt gagccttctg tgcctgcagA TGCTAGGTAA CAAGCGACTG GGGCTGTCCG
61  GACTGACCCT CGCCCTGTCC CTGCTCGTGT GCCTGGGTGC GCTGGCCGAG GCGTACCCCT
121 CCAAGCCGGA CAACCCGGGC GAGGACGCAC CAGCGGAGGA CATGGCCAGA TACTACTCAG
181 CGCTGGGACA CTACATCAAC CTCATCACCA GGCAGAGgtg ggtgggaccg cgggaccgat
241 tccggga
```

SEQ ID NO:3 (M14297)

```
1   acttgctttta aaagactttt ttttttccag ATATGGAAAA CGATCTAGCC CAGAGACACT
61  GATTTCAGAC CTCTTGATGA GAGAAAGCAC AGAAAATGTT CCCAGAACTC Ggtatgacaa
121 ggcttgtgat ggggacattg tt
```

SEQ ID NO:4 (M14298)

```
1   CCTTACATGC TTTGCTTCTT ATGTTTTACA Ggcttgaaga ccctgcaatg tggtgatggg
61  aaatgagact tgctctctgg ccttttccta ttttcagccc atatttcatc gtgtaaaacg
121 agaatccacc catcctacca atgcatgcag ccactgtgct gaattctgca atgttttcct
181 ttgtcatcat tgtatatatg tgtgtttaaa taagtatca tgcattcaaa agtgtatcct
241 cctcaatgaa aaatctatta caatagtgag gattattttc gttaaactta ttattaacaa
```

FIG. 1B

HUMAN NEUROPEPTIDE Y (NPY) mRNA

SEQ ID NO:5 (K01911)

```
                                                          C
                                                          ↓
1    accccatccg ctggctctca ccctcggag acgctcgccc gacagcatag tacttgccgc
61   ccagccacgc ccgcgcgcca gccaccatgc taggtaacaa gcgacggggg ctgtccggac
121  tgaccctcgc cctgtccctg ctcgtgtgcc tgggtgcgct ggccgaggcg tacccctcca
181  agccggacaa cccgggcgag gacgcaccag cggaggacat ggccagatac tactcggcgc
241  tgcgacacta catcaacctc atcaccaggc agagatatgg aaaacgatcc agcccagaga
301  cactgatttc agacctcttg atgagagaaa gcacagaaaa tgttcccaga actcggcttg
361  aagaccctgc aatgtggtga tgggaaatga gacttgctct ctggcctttt cctattttca
421  gcccatattt catcgtgtaa aacgagaatc cacccatcct accaatgcat gcagccactg
481  tgctgaattc tgcaatgttt cctttgtca tcattgtata tatgtgtgtt taaataaagt
541  atcatgcatt c
```

FIG. 1C

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 325 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
CCGCTTCTTC AGGCAGTGCC TGGGGCGGGA GGGTTGGGGT GTGGGTGGCT CCCTAAGTCG      60

ACACTCGTGC GGCTGCGGTT CCAGCCCCCT CCCCCCGCCA CTCAGGGGCG GGAAGTGGCG     120

GGTGGGAGTC ACCCAAGCGT GACTGCCCGA GGCCCCTCCT GCCGCGGCGA GGAAGCTCCA     180

TAAAAGCCCT GTCGCGACCC GCTCTCTGCA CCCCATCCGC TGGCTCTCAC CCCTCGGAGA     240

CGCTCGCCCG ACAGCATAGT ACTTGCCGCC CAGCCACGCC CGCGCGCCAG CCACCGTGAG     300

TGCTACGACC CGTCTGTCTA GGGGT                                          325
```

(2) INFORMATION FOR SEQ ID NO:2:

(i) SEQUENCE CHARACTERISTICS:
      (A) LENGTH: 247 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:2:

```
CCCGTCCGTT GAGCCTTCTG TGCCTGCAGA TGCTAGGTAA CAAGCGACTG GGGCTGTCCG      60

GACTGACCCT CGCCCTGTCC CTGCTCGTGT GCCTGGGTGC GCTGGCCGAG GCGTACCCCT     120

CCAAGCCGGA CAACCCGGGC GAGGACGCAC CAGCGGAGGA CATGGCCAGA TACTACTCAG     180

CGCTGCGACA CTACATCAAC CTCATCACCA GGCAGAGGTG GGTGGGACCG CGGGACCGAT     240

TCCGGGA                                                              247
```

(2) INFORMATION FOR SEQ ID NO:3:

(i) SEQUENCE CHARACTERISTICS:
      (A) LENGTH: 142 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:3:

```
ACTTGCTTTA AAAGACTTTT TTTTTTCCAG ATATGGAAAA CGATCTAGCC CAGAGACACT      60

GATTTCAGAC CTCTTGATGA GAGAAAGCAC AGAAAATGTT CCCAGAACTC GGTATGACAA     120

GGCTTGTGAT GGGGACATTG TT                                             142
```

(2) INFORMATION FOR SEQ ID NO:4:

(i) SEQUENCE CHARACTERISTICS:
      (A) LENGTH: 300 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
CCTTACATGC TTTGCTTCTT ATGTTTTACA GGCTTGAAGA CCCTGCAATG TGGTGATGGG      60

AAATGAGACT TGCTCTCTGG CCTTTTCCTA TTTTCAGCCC ATATTTCATC GTGTAAAACG     120

AGAATCCACC CATCCTACCA ATGCATGCAG CCACTGTGCT GAATTCTGCA ATGTTTTCCT     180

TTGTCATCAT TGTATATATG TGTGTTTAAA TAAAGTATCA TGCATTCAAA AGTGTATCCT     240

CCTCAATGAA AAATCTATTA CAATAGTGAG GATTATTTTC GTTAAACTTA TTATTAACAA     300
```

(2) INFORMATION FOR SEQ ID NO:5:

(i) SEQUENCE CHARACTERISTICS:
        (A) LENGTH: 551 base pairs
        (B) TYPE: nucleic acid
        (C) STRANDEDNESS: single
        (D) TOPOLOGY: linear (ii) MOLECULE TYPE: mRNA (ix) FEATURE:
        (A) NAME/KEY: sig_peptide
        (B) LOCATION: 87..170

(ix) FEATURE:
        (A) NAME/KEY: CDS
        (B) LOCATION: 87..377

(xi) SEQUENCE DESCRIPTION: SEQ ID NO:5:

```
ACCCCATCCG CTGGCTCTCA CCCCTCGGAG ACGCTCGCCC GACAGCATAG TACTTGCCGC      60

CCAGCCACGC CCGCGCGCCA GCCACC ATG CTA GGT AAC AAG CGA CTG GGG CTG     113
                              Met Leu Gly Asn Lys Arg Leu Gly Leu
                                1               5

TCC GGA CTG ACC CTC GCC CTG TCC CTG CTC GTG TGC CTG GGT GCG CTG     161
Ser Gly Leu Thr Leu Ala Leu Ser Leu Leu Val Cys Leu Gly Ala Leu
 10              15                  20                  25

GCC GAG GCG TAC CCC TCC AAG CCG GAC AAC CCG GGC GAG GAC GCA CCA     209
Ala Glu Ala Tyr Pro Ser Lys Pro Asp Asn Pro Gly Glu Asp Ala Pro
                 30                  35                  40

GCG GAG GAC ATG GCC AGA TAC TAC TCG GCG CTG CGA CAC TAC ATC AAC     257
Ala Glu Asp Met Ala Arg Tyr Tyr Ser Ala Leu Arg His Tyr Ile Asn
             45                  50                  55

CTC ATC ACC AGG CAG AGA TAT GGA AAA CGA TCC AGC CCA GAG ACA CTG     305
Leu Ile Thr Arg Gln Arg Tyr Gly Lys Arg Ser Ser Pro Glu Thr Leu
         60                  65                  70

ATT TCA GAC CTC TTG ATG AGA GAA AGC ACA GAA AAT GTT CCC AGA ACT     353
Ile Ser Asp Leu Leu Met Arg Glu Ser Thr Glu Asn Val Pro Arg Thr
     75                  80                  85

CGG CTT GAA GAC CCT GCA ATG TGG TGATGGGAAA TGAGACTTGC TCTCTGGCCT     407
Arg Leu Glu Asp Pro Ala Met Trp
 90                  95

TTTCCTATTT TCAGCCCATA TTTCATCGTG TAAAACGAGA ATCCACCCAT CCTACCAATG     467

CATGCAGCCA CTGTGCTGAA TTCTGCAATG TTTTCCTTTG TCATCATTGT ATATATGTGT     527

GTTTAAATAA AGTATCATGC ATTC                                            551
```

(2) INFORMATION FOR SEQ ID NO:6:

(i) SEQUENCE CHARACTERISTICS:

(A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO:6:

Met Leu Gly Asn Lys Arg Leu Gly Leu Ser Gly Leu Thr Leu Ala Leu
 1               5                  10                  15

Ser Leu Leu Val Cys Leu Gly Ala Leu Ala Glu Ala Tyr Pro Ser Lys
             20                  25                  30

Pro Asp Asn Pro Gly Glu Asp Ala Pro Ala Glu Asp Met Ala Arg Tyr
             35                  40                  45

Tyr Ser Ala Leu Arg His Tyr Ile Asn Leu Ile Thr Arg Gln Arg Tyr
     50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                 85                  90                  95

Trp (2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

TTGGGGTGTG GGTGGCTC                                                        18

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

CCTAGACAGA CGGGTCGTAG CA                                                   22

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

CCCGTCCGTT GAGCCTTCTG                                                      20

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

CGGTCCCGCG GTCCC                                                    15

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

AAAAGACTTT TTTTTTTCCA G                                             21

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

AATGTCCCCA TCACAAG                                                  17

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

CCTTACATGC TTTGCTTCTT A                                             21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

GATTTTTCAT TGAGGAGGAT                                               20

DNA MOLECULE ENCODING A MUTANT PREPRO-NEUROPEPTIDE Y, A MUTANT SIGNAL PEPTIDE, AND USES THEREOF

FIELD OF THE INVENTION

This invention relates to a DNA sequence encoding a mutant human prepro-neuropeptide Y (preproNPY), the mutant signal peptide as such or associated with any other cleavage product of preproNPY, methods for the determination, in a biological sample, of said DNA sequence or said peptide. Furthermore, this invention relates to a method for diagnosing a predisposition for increased serum cholesterol or LDL cholesterol in a human subject, and to methods for treating a human subject diagnosed for predisposition for increased serum cholesterol or LDL cholesterol. Transgenic animals carrying either the mutant sequence or the normal sequence are also within the scope of this invention.

BACKGROUND OF THE INVENTION

The publications and other materials used herein to illuminate the background of the invention, and in particular, cases to provide additional details respecting the practice, are incorporated by reference.

Neuropeptide Y (NPY) is a 36-amino-acid peptide hormone abundantly expressed both in the central and peripheral nervous systems. NPY plays a central role in the hypothalamic regulation of food intake and energy expenditure. Central administration of NPY markedly stimulates feeding, and chronic infusion results in development of obesity, hyperinsulinemia and insulin resistance in experimental animals. Relatively little is known of the role of NPY in human obesity or metabolic diseases.

Neuropeptide Y (NPY), a member of a family of peptides, is a neurotransmitter, which is widely expressed both in the central and peripheral nervous systems[1,2]. Several regulatory functions have been implicated to NPY including feeding[3,4,5], anxiolysis[6,7], pituitary hormone release[8,9,10], thermogenesis[11] and insulin release[12].

In animals NPY plays an important role in the hypothalamic regulation of energy balance. NPY markedly stimulates food intake after central administration[13]. It also decreases energy expenditure by decreasing brown adipose tissue thermogenesis, and favors energy storage by increasing lipoprotein lipase activity in white adipose tissue[14]. Chronic intracerebroventricular infusion of NPY results in the development of obesity and insulin resistance[13]. Food restriction markedly enhances hypothalamic NPY activity, while re-feeding decreases it, and the hypothalamic NPY neurons are controlled by peripheral hormonal feedback signals, like insulin and leptin[14,15,16]. Consequently, hypothalamic expression of preproNPY mRNA and NPY levels are elevated in obese fa/fa Zucker rat[17], which have impaired leptin signaling due to a point mutation in the leptin receptor gene[18]. In humans, NPY concentrations in the cerebrospinal fluid of anorexia patients are elevated[19], which is consistent with the putative compensatory activation of NPY mechanisms. Importantly anorexia patients also show elevated cholesterol levels[20,21]. However no reports were available from the literature connecting NPY gene or NPY as such to cholesterol metabolism or serum cholesterol levels.

SUMMARY OF THE INVENTION

According to one aspect, this invention concerns a DNA sequence comprising a nucleotide sequence encoding a prepro-neuropeptide Y (preproNPY) where the leucine amino acid in position 7 of the signal peptide part of said preproNPY has been replaced by proline.

According to a second aspect, the invention concerns a method for screening a subject to determine if said subject is a carrier of a mutant NPY gene, comprising the steps of providing a biological sample of the subject to be screened; and providing an assay for detecting in the biological sample the presence of i) the normal NPY gene or II) the mutant NPY gene.

According to a third aspect, the invention concerns a signal peptide having the leucine in the 7 position replaced by proline, and said signal peptide associated with any other cleavage product of preproNPY.

According to a fourth aspect, this invention concerns an antibody capable of binding said signal peptide or said signal peptide associated with any other cleavage product of preproNPY, and to an immunoassay for the determination of said peptide in a biological sample.

According to a fifth aspect, the invention concerns a method for diagnosing a predisposition for increased serum cholesterol or LDL cholesterol level in a human subject, said method comprising determining whether said subject has a polymorphism in the signal peptide part of the human preproNPY, said polymorphism comprising the substitution of the position 7 leucine for proline in the signal peptide part of said preproNPY, said polymorphism being indicative of a predisposition to increased serum cholesterol or LDL cholesterol level.

According to a sixth aspect, the invention relates to a method for treating a human subject, diagnosed for predisposition increased serum cholesterol or LDL cholesterol level, for the prevention of increased serum cholesterol or LDL cholesterol level in said subject comprising administering to said subject an effective amount of an agent counteracting the influence of the mutated NPY gene.

According to a seventh aspect, the invention relates to a method for treating a human subject, diagnosed for predisposition of increased serum cholesterol or LDL cholesterol levels, for the prevention of increased serum cholesterol or LDL cholesterol levels in said subject comprising subjecting the person to specific gene therapy aimed to repair the mutated NPY sequence.

According to still one aspect, the invention concerns a transgenic animal which carries a human DNA sequence comprising a nucleotide sequence encoding a prepro-neuropeptide Y (preproNPY) where the leucine amino acid in position 7 of the signal peptide part of said preproNPY is i) either replaced by proline, or ii) is unchanged.

According to still one aspect, the invention concerns a transgenic animal which carries a DNA sequence comprising a nucleotide sequence encoding otherwise normal mouse NPY sequence or part thereof encoding mature mouse NPY peptide, but in which the nucleotide sequence encoding the mouse signal peptide is replaced by human signal peptide sequence encoding either normal or mutated human signal peptide.

According to still one aspect, the invention concerns a cell line expressing the mutated human NPY gene or part thereof.

BRIEF DESCRIPTION OF THE DRAWINGS

FIG. 1b shows the nucleotide sequence of the human NPY gene. Upper case indicates exonic sequences land lower case intronic sequences. Genbank accession numbers are given in parenthesis. The arrow shows the position in which T of the normal gene is replaced by C to give the mutant gene. The underlined sequence in Exon 2 is the sequence encoding the signal peptide of 28 amino acids. Exon 1 is SEQ ID NO:1, exon 2 is SEQ ID NO:2, exon 3 is SEQ ID NO:3 and exon 4 is SEQ ID NO:4.

FIG. 1c shows the nucleotide sequence of the human preproNPY mRNA (SEQ ID NO:5, with the protein sequence set forth in SEQ ID NO:6). The arrow shows the position in which + of the normal mRNA is replaced by +c to give the mutant mRNA.

DETAILED DESCRIPTION OF THE INVENTION

Figure 1A:
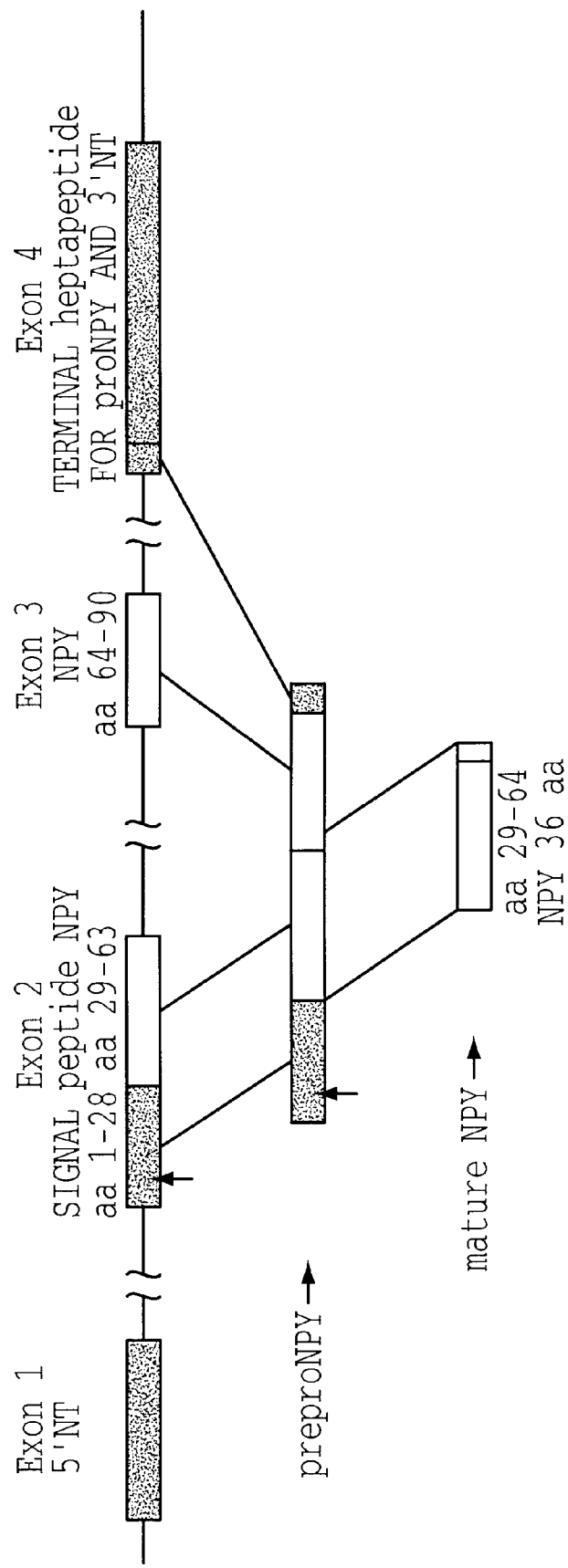
FIG. 1a illustrates schematically the molecular structure of the human NPY gene, the preproNPY peptide and the mature NPY peptide.
Figure 2A:
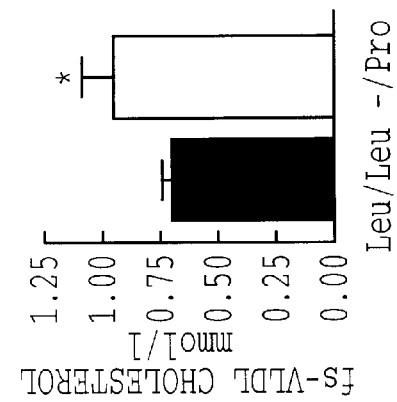
FIG. 2 shows a) the fasting serum total cholesterol, b) LDL-cholesterol, c) HDL-cholesterol and d) VLDL-cholesterol in obese subjects, where the filled bars represent subjects (n=120) homozygous to Leu7/Leu7 of the signal peptide of the preproNPY and the empty bars represent subjects (n=21) heterozygous to Leu7/Pro7or homozygous to Pro7/Pro7 in the signal peptide of the preproNPY.
Figure 2B:
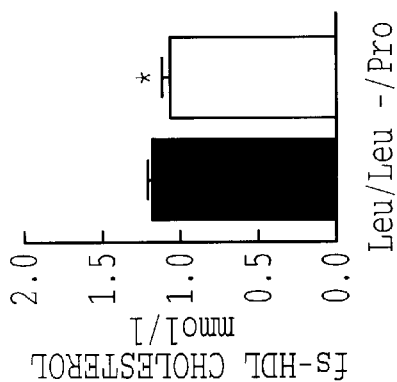
Figure 2C:
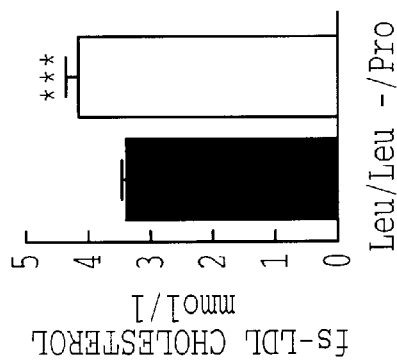
Figure 2D:
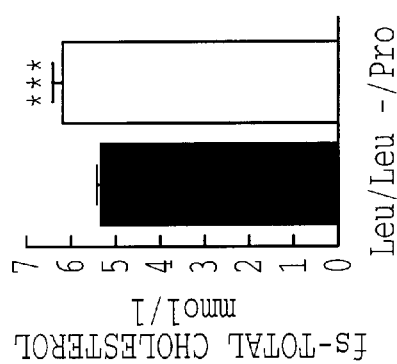
Figure 3D:
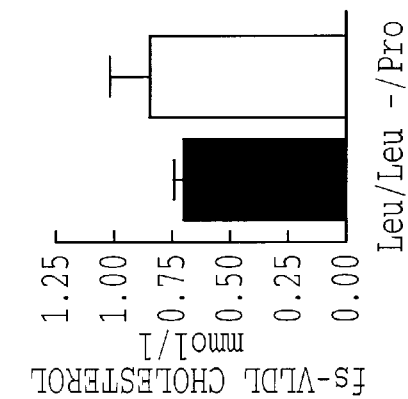
FIG. 3 shows a) the fasting serum total cholesterol, b) LDL-cholesterol, c) HDL-cholesterol and d) VLDL-cholesterol in normal weight subjects, where the filled bars represent subjects (n=56) homozygous to Leu7/Leu7 of the signal peptide of the preproNPY and the empty bars represent subjects (n=8) heterozygous to Leu7/Pro7 or homozygous to Pro7/Pro7 in the signal peptide of the preproNPY.
Figure 3C:
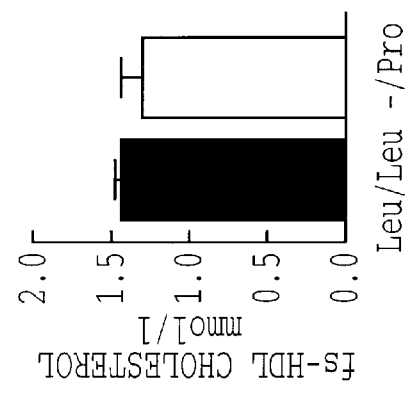
Figure 3B:
Figure 3A:
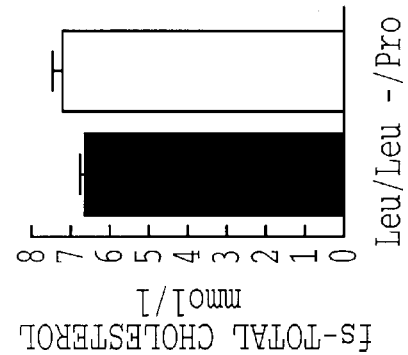

The present invention is a part of the inventors' study program to investigate the genetic background of energy metabolism and obesity. We report here the identification of a rather common polymorphism in the signal peptide part of the NPY gene. Surprisingly, this Leu7 to Pro polymorphism was found to associate with significant elevation of both total and LDL cholesterol levels in normal weight and obese, non-diabetic subjects, while it was not related with energy metabolism or obesity.

The DNA sequence or the mutant signal peptide or said peptide associated with any other cleavage product of pre-proNPY can be used for screening a subject to determine if said subject is a carrier of a mutant NPY gene.

The determination can be carried out either as a DNA analyse according to well known methods, which include direct DNA sequencing of the normal and mutated NPY gene, allele specific amplification using the polymerase chain reaction (PCR) enabling detection of either normal or mutated NPY sequence, or by indirect detection of the normal or mutated NPY gene by various molecular biology methods including e.g. PCR-single stranded conformation polymorphism (SSCP)-method or denaturing gradient gel electrophoresis (DGGE). Determination of the normal or mutated NPY gene can also be done by using restriction fragment length polymorphism (RFLP)-method, which is particularly suitable for genotyping large number of samples.

The determination can also be carried out at the level of RNA by analysing RNA expressed at tissue level using various methods. Allele specific probes can be designed for hybridization. Hybridization can be done e.g. using Northern blot, RNase protection assay or in situ hybridization methods. RNA derived from the normal or mutated NPY gene can also be analysed by converting tissue RNA first to cDNA and thereafter amplifying cDNA by an allele specific PCR-method.

Alternatively, the determination can be carried out as an immunoassay where a sample is contacted with an antibody capable of binding the signal peptide or said peptide associated with any other cleavage product of preproNPY.

Antibodies can be raised against normal or mutated preproNPY or more specifically against normal or mutated signal peptide part of the NPY. The production of antibodies can be done in experimental animals in vivo to obtain polyclonal antibodies or in vitro using cell lines to obtain monoclonal antibodies.

A human subject, diagnosed for predisposition of increased serum cholesterol or LDL cholesterol levels, can be treated for the prevention of increased serum cholesterol or LDL cholesterol in said subject by administering to said subject an effective amount of an agent counteracting the influence of the mutated NPY gene. This can be done by specific gene therapy aimed to repair the mutated NPY sequence, or by administering pharmacotherapies, which are aimed to modulate synthesis, release or metabolism of the endogenous NPY, or to interact in a specific manner at NPY target sites by modulating effects of NPY with specific NPY receptor proteins. Currently, five different subtypes of NPY receptors have been cloned and characterized (Y1–Y5 receptors) and drug molecules specifically interacting with these NPY receptors have been synthesized. The pharmacotherapy described is not limited to only these named receptors or mechanisms, but also covers other NPY receptors and related mechanisms to be discovered.

Influence of the mutated NPY sequence on the function of NPY gene can be investigated in transgenic animals. A transgenic animal can be generated using targeted homologous recombination methodology. Both normal and mutated sequence of human NPY signal peptide (or any DNA sequence comprising a nucleotide sequence encoding a prepro-neuropeptide Y (preproNPY) or part thereof encoding the amino acid sequence of the mature mouse or human mature NPY peptide, where either i) the leucine amino acid in position 7 of the signal peptide part of said preproNPY has been replaced by proline or ii) the leucine amino acid in position 7 of the signal peptide part of said preproNPY is unchanged) will be introduced into the sequence of NPY gene to replace the endogenous signal peptide sequence. Under these conditions, the endogenous NPY gene functions otherwise normally, but the synthesis of the preproNPY is regulated by either normal or mutated human NPY signal peptide sequence. This transgenic model can be used to investigate in a very specific manner the physiological importance of the mutated NPY gene. It also will provide an ideal preclinical model to investigate and screen new drug molecules, which are designed to modify the influence of the mutated NPY gene.

The invention is described more in detail in the following experiments.

EXPERIMENTS

Methods

Coding regions of the NPY gene were screened for possible sequence variants in 90 Finnish obese subjects using the single-stranded conformation polymorphism (SSCP)-analysis. Allelic associations of the identified Leu7 to Pro polymorphism with obesity-related and metabolic parameters were analyzed in two independent study populations after genotyping 141 obese, non-diabetic subjects (study I) and 64 normal weight subjects (study II) using the restriction length polymorphism (RFLP) method.

Study subjects for SSCP screening of the NPY gene

The DNA samples from 90 randomly selected obese Finns of the study I population were used to screen NPY gene for exonic sequence variants.

Study subjects for association and genotype frequency analyses

Study I 141 (29 men and 112 women) obese subjects of a weight reduction study (Uusitupa et al. 1996) with a normal liver, kidney and thyroid function were included in the association study of NPY sequence variant with phenotype parameters. None of the subjects had diabetes, history of excessive alcohol intake or taking drugs known to affect basal metabolic rate (BMR), cholesterol (except one subject that was on a betablocking agent) or glucose metabolsim. Their mean±SD age was 43±8 years and the mean body mass index (BMI) 34.7, range 28–43 kg/m². All phenotype measurements were done in the morning after a 12-h fast by standardized methods. The measurements included weight, BMI, percental fat, respiratory quotient (RQ), BMR, waist-to-hip ratio (WHR), fasting serum leptin, glucose, insulin, cholesterol and triglyceride levels. The main characteristics of the study I subjects are presented in Table 1. The analytical methods have been described elsewhere in detail[22,23]. A diet diary was available of all obese subjects with detailed data on the daily intake of several nutrients including carbohydrate, protein, fat and cholesterol.

Study II

Originally a random control population sample, aged 45–64 years, was selected during 1979–1981 from the population registers of the Kuopio county, Finland by using random number tables, taking into account the distribution of the population living in rural and urban communities. Of 183 subjects originally contacted, finally 144 were recruited. The normal weight (BMI<27 kg/m²) subjects were selected among the control subjects for the present investigation (study II) and they were followed for 10 years. Altogether 64 (26 men and 38 women) normoglycemic, non-diabetic healthy Finns were examined. The control subjects were re-examined after 5 and 10 years from the first examination in the years 1985–1986 and 1991–1992, respectively. The main characteristics of the study II population in these respective time point are presented in Table 2. The protocol was approved by the Ethics Committees of the University of Kuopio and Helsinki. The study II population has been described in detail previously[24].

PCR-SSCP analysis

The human NPY gene is divided into four exons, the first containing nontranslated region, the second exon coding signal peptide (amino acid residues 1–28) and mature NPY amino acid residues 29–63, the third exon coding residues 64–90, and the fourth exon contains the carboxy terminal heptapeptide of proNPY and the nontranslated 3'-region FIG. 1a)[25]. The PCR pimer pairs and the respective PCR annealing temperatures (Ta) for amplification of the four exonic areas of the NPY gene were as follows: Pair 1 5' TTGGGGTGTGGGTGGCTC (SEQ ID NO:7) and 5' CCTAGACAGACGGGTCGTAGCA, (SEQ ID NO:8) at Ta=65° C., pair 2 5' CCCGTCCGTTGAGCC TTCTG (SEQ ID NO:9) and 5' CGGTCCCGCGGTCCC (SEQ ID NO:10) Ta=67° C.), pair 3 5' AAAAGACTTTTTTT TTTCCAG (SEQ ID NO:11) and 5' AATGTCCCCATCACAAG (SEQ ID NO:12) Ta=51° C., and pair 4 5' CCTTACAT GCTTTGCTTCTTA (SEQ ID NO:13) and 5' GATTTTTCATTGAGGAGGAT at Ta=51° C. The PCR reaction (total 5 µl) contained 100 ng genomic DNA (isolated either from whole blood or immortalized lymphoblast cell liens), 1.0 mM dNTPs, 30 nM $^{33}$P-dCTP, 2.5 mM each primer, 0.25 U of AmpliTaq polymerase (Perkin Elmer Cetus, Norwalk, Conn.). PCR conditions were optimized using PCR Optimizer™ (Invitrogen, San Diego, Calif.). Samples were amplified with a GeneAmp PCR System 9600 (Perkin Elmer Cetus, Norwalk, Conn.), 30 cycles consisting for 30 sec at 94° C., 30 sec at optimal annealing temperature and 30 sec at 72° C. This was followed by an elongation step 7 min at 72°. The amplified samples were mixed with SSCP buffer containing 95% formamide, 10 mM NaOH, 0.05% xylene cyanol and 0.05% bromphenol blue (total volume of 25 µl). Prior to loading, samples were denatured 5 min at 95° C. and kept 5 min on ice. Three µl of the mixture was loaded on a MDE™ gel (FMC, BioProducts, Rockland, Mass.). The SSCP-gel electrophoresis was performed at two different running conditions: 6% MDE gel at +4° C. and 3% MDE gel with 10% glycerol at room temperature. Electrophoresis was run at 5 W constant power for 20 hr. The gel was dried and autoradiography was performed by exposing a Kodak BIO MAX MR film for 24 hours at room temperature.

Sequencing

The abnormally migrating bands in SSCP were sequenced with the Thermo Cycle Sequenase™ kit (Amersham Life Science, Inc. Cleveland, Ohio).

Genotyping

The primers used for genotyping of subjects in study I and II were those used for the exon 2 PCR amplification. In the exon 2 the T(1128) to C(1128) substitution generates an Bsi E I (New England Biolabs, Inc. Beverly, Mass.) site. Digestions were analyzed by electrophoresis in 2% agarose gel.

Fasting serum parameters and anthoropometric measurements

Blood glucose was analyzed by the glucose-oxidase method (Glox: Kabi Ab, Stockholm, Sweden). Serum insulin was analyzed by radioimmunoassay (antiserum M 8309: Novo Industries, Copenhagen, Denmark). The variation coefficient of the method was 5.4%, and the sensitivity was 2 mU/l. Serum and lipoprotein lipids were determined from 12-h fasting samples. Lipoproteins were separated by ultracentrifugation at density 1.006 to remove VLDL, followed by precipitation of the infranatant fraction by dextran sulphate and magnesium chloride[26]. Enzymatic methods were used for the determination of cholesterol[27] and triglycerides[28] from whole serum, the top layer after ultracentrifugation of VLDL, and the supernatant after precipitation of LDL. LDL was calculated as the difference between whole serum and the sum of VLDL and HDL. The intra-assay variation for total cholesterol, HDL cholesterol, and triglycerides was 1.3%, 0.95%, and 3.1% respectively, and the interassay variation was 3.3%, 1.9%, and 5.2%, respectively. Standing height was measured without shoes to the nearest 0.5 cm. Body weight was measured with an electric weighing machine (model 707: Seca. Hamburg, Germany) with the subjects barefoot and dressed in shorts. Body mass index (BMI) was calculated (body weight[kg]/height[m²]). For the waist/hip ratio the waist circumference was measured at the level of the midway between the lateral lower rib margins and the iliac crest. Hip circumference was measured at the level of the greater trochanters through the pubic symphysis. Resting energy expenditure was measured by indirect calorimetry (Deltatrac,™ Datex, Helsinki, Finland) using a computerterized flow-through, canopy-gas analyzer system, which was calibrated with the precision gas mixture before each measurement. The method of described previously in detail[29].

Statistical analysis

The genotype frequency distribution was tested for Hardy-Weinberg equilibrium by $X^2$-analysis. All calculations concerning the association analysis were performed using the SPSS/WIN program version 6.0 (SPSS, Chicago, Ill.). Statistical differences in phenotype parameters between the two groups were evaluated using the Student's t test. In study I multiple comparisons between the genotype and phenotype parameters were done without a formal correction for multiple testing. In the study II, we had an a priori hypothesis that the polymorphism associates with serum cholesterol level, and therefore no other statistical comparisons were carried out than that of fasting serum total, LDL, HDL and VLDL cholesterol levels.

RESULTS

The SSCP screening resulted in detection of thymidine (1128) to cytosine substitution leading to leucine to proline amino acid change at the residue 7, of the hydrophobic signal peptide part of the preproNPY. The allele frequency of the Leu7 to Pro polymorphism was 0.08 for both normal weight and obese subjects. The obese subjects having the Pro7 allele had significantly higher fasting serum total, LDL and VLDL cholesterol levels and lower HDL cholesterol level, when compared to corresponding values in subjects with the Leu/Leu7 genotype. The respective values were 6.2±1.1 vs. 5.3±0.9 mmol/l (P=0.0001), 4.2±1.0 vs. 3.5±0.8 mmol/l (P=0.0003), 0.9±0.6 vs. 0.7±0.5 mmol/l (P=0.042) and 1.1±0.3 vs. 1.2±0.3 mmol/l (P=0.041). These differences could not be explained by confounding factors including age, sex, smoking, concomitant medication or the apoE-phenotypes. The Leu7 to Pro polymorphism in the NPY gene did not associate with any obesity related parameter including weight, BMI, waist-to-hip ratio, fat mass, basal metabolic rate or other metabolic parameters such as fasting plasma levels of glucose, insulin, leptin or triglycerides in obese subjects. The significant association of the Pro7 allele with higher serum total cholesterol (p=0.35) and LDL-cholesterol levels (p=0.036) was confirmed in normal weight subjects of the study II.

SSCP screening of the exonic areas of the NPY gene

Individual exons comprising the whole coding region of the NPY gene were screened for mutations by SSCP. The identified polymorphism were 1)T(1128) to C(1128), 2)A (1258) to G(1258), 3)T(5671) to C(5671), and 4)T(8233) to A(8233). The numbering of the polymorphism is according to the Minth et al. 1986, in which the polymorphism 2 and 3 were already reported[25].

Genotype frequencies

All the allelic frequencies are in Hardy-Weinberg equilibrium. The allele frequency of the found T(1128) to C(1128) polymorphism were 0.078 in obese (n=141) and 0.077 in normal weight control Finns (n=64). There were no differences in any of the allelic distributions between these two populations.

Association analysis

Study I:

The homozygote Pro7/Pro7 genotype was detected in only one subject, who was included to the heterozygote group. The association analysis between the Pro7/Leu7 genotype subjects (including one Pro7/Pro7 genotype) and the wild type Leu7/Leu7 genotype subjects revealed highly significant differences in fasting serum total cholesterol 6.2±1.1 vs. 5.3±0.9 mmol/l (P=0.0001), LDL cholesterol 4.2±1.0 vs. 3.5±0.8 mmol/l (P=0.0003), and VLDL cholesterol 0.9±0.6 vs. 0.7±0.5 mmol/l (P=0.042) levels and HDL cholesterol 1.1±0.3 vs. 1.2±0.3 mmol/l (P=0.041) (FIG. 2.) The differences remained highly significant if the analysis was performed separately in obese men (total-cholesterol, LDL cholesterol, VLDLcholesterol and HDL cholesterol) and in obese women (total cholesterol and LDL cholesterol). The intake of total fat, saturated fatty acids, unsaturated fatty acids or dietary cholesterol did not differ in the two genotype group. The degree of obesity does not explain these findings, either. There were no differences in the distribution of apolipoprotein-E phenotypes between the different groups (data not shown).

Study II:

One subject was homozygote Pro7/Pro7 and was analyzed together with the heterozygotes. In normal weight subjects the fasting serum total and LDL cholesterol levels were significantly higher in subjects having the Pro7 allele than in subjects with the Leu7/Leu7 genotype of every three measurement. Fasting serum total cholesterol 7.4±0.6 vs. 6.7±0.9 mmol/l (P=0.035). LDL cholesterol 5.2±0.6 vs. 4.5±0.9 mmol/l (P=0.036). There were no statistically significant differences in VLDL cholesterol (0.8±0.5 vs. 0.7±0.4 mmol/l) or HDL cholesterol (1.3±0.4 vs. 1.5±0.3 mmol/l levels) (FIG. 3).

DISCUSSION

The present study provides the first evidence that the Leu7 to Pro polymorphism in NPY gene associates with clinically unfavorable serum cholesterol and LDL cholesterol levels both in normal weight and non-diabetic obese subjects. This indicates that NPY may have a previously unrecognized role in the regulation of cholesterol metabolism in human and is one of the strongest genetic factors thus far identified affecting serum cholesterol levels.

The major observation of the present study is that the identified polymorphism leucine7 to proline in the signal peptide part of the NPY gene significantly associates with elevated serum total and LDL cholesterol levels in Finns. Furthermore, in obese subjects also VLDL cholesterol was significantly increased and HDL cholesterol decreased in subjects with the Pro7 allele. The main finding was initially done in obese, non-diabetic subjects, and was subsequently repeated in normal weight subjects. The allele frequency of this sequence variant was about 8% in the Finnish populations. The observed association cannot be explained by other confounding factors known to affect cholesterol metabolism, such as age, obesity, sex, smoking, drugs or the apoE phenotype. Furthermore, it is also highly unlikely that the association could be due to a stratification error in the study subjects, since they all were native Finns with rather similar genetic background. Thus, leucine7 to proline polymorphism of the NPY gene should be considered as an important new genetic marker for high serum total cholesterol and LDL cholesterol levels.

The leucine7 to proline polymorphism is located in the signal peptide part of the preproNPY. The signal peptide, which is cleaved away from the mature NPY, plays an important role by guiding proper folding and packing of the peptide in the endoplasmic reticulum during the synthesis and transport into secretory vesicles. Usually the signal peptide consists of a hydrophobic motif as is the case with preproNPY. Leucine is known to form α-helices, while proline usually introduces breaks and kinks into α-helical parts of the peptide backbone. Although we do not have biochemical data how the leucine7 to proline polymorphism modifies the synthesis of the preproNPY, one could speculate that intracellular processing of preproNPY synthesis is impaired, which subsequently could lead to altered NPY activity. However, further studies are required to elucidate these mechanism in detail.

Serum total cholesterol and LDL cholesterol levels were on average 0.9 and 0.7 mmol/l, respectively, higher in obese and non-obese Finnish subjects having the Pro7 allele compared to those having Leu7/Leu7 genotype. Moreover, a trend to a higher VLDL cholesterol and lower HDL cholesterol were found in these subjects. The impact of this genetic abnormality on serum cholesterol level is greater than that of apo E 4 allele[30], and is of the same magnitude (14%) that could be obtained at best by cholesterol lowering diet therapy in free living Finnish subjects.

What are then the reasons for the elevation of serum total and LDL cholesterol in these subjects representing of 8% of Finnish population?. Due to fact that gastrointestinal tract is abundantly innervated by NPY containing nerves[31,32] one can speculate that NPY could be involved in the absorption of dietary cholesterol, and subjects with the Pro7 allele might have an increased cholesterol absorption. This, on the other hand, could result in down-regulation of B/E (LDL) receptor activity of the liver and an elevation of LDL and its precursors in serum, e.g. VLDL. Because there were no marked abnormalities in VLDL or triglyceride levels in the affected subjects we consider that the primary defect can not be in the synthesis or the catabolism of VLDL. Interestingly, however, central NPY increases the expression of lipoprotein lipase mRNA and enhances the enzyme activity in white fat favoring lipid storage. Therefore, the role of lipoprotein lipase activity can not be totally excluded. The most plausible explanation for the elevation of serum cholesterol levels is, however, diminished amount of activity of LDL receptors which are known to regulate the serum concentration of LDL, and to a lesser degree, of LDL and VLDL particles as well. Obesity as such does not seem to modify the impact of the leucine7 to proline polymorphism on serum lipids since the differences in lipid values between the mutated and normal subjects were similar in obese and normal weight subjects. After all, it should be noticed that there is no experimental evidence to support any of these mechanisms discussed above which could link this particular genetic abnormality in NPY to cholesterol metabolism.

As said before ApoE-phenotype 4 is also known to associate with higher serum total cholesterol and LDL-cholesterol levels, which has previously reported in our study subjects[22]. The apoE-phenotype 4 was evenly distributed in both NPY groups and does not confound the association of the NPY signal peptide polymorphism with differences in serum cholesterol levels.

The identified leucine7 to proline polymorphism in the NPY gene did not seem to associate in the present study to any obesity related parameters, like weight, BMI, WHR, BMR or RQ. In agreement, the allele frequencies of the mutated allele were similar in normal weight controls and obese, non-diabetic subjects. This result is also consistent with a recent study performed in a French population, in which flanking markers of the NPY gene failed to be in linkage with any traits of obesity[33].

The present study provides the first evidence that the leucine7 to proline polymorphism in NPY gene associates with clinically unfavorable serum cholesterol and lipoprotein levels both in non-diabetic normal weight and obese subjects. This indicates that NPY may have a previously unknown role in the control of cholesterol metabolism in man and is one of the strongest genetic factors thus far identified affecting serum cholesterol levels. Furthermore, NPY mechanisms could offer potential targets to the development of new drugs.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

TABLE 1

Demogaphic and clinical characteristics of 141 obese subjects according to the presence or absence of the Leu(7) to Pro(7) mutation in the NPY gene. The values are mean ± SD.

| Characteristic | Without mutation | With mutation | P value |
|---|---|---|---|
| age, years | 40.7 ± 6.2 | 4.12 ± 8.1 | ns |
| sex, F/M | 95/25 | 17/4 | ns |
| BMI, kg/m² | 34.7 ± 3.8 | 35.7 ± 3.3 | ns |
| WHR | 0.93 ± 0.08 | 0.94 ± 0.08 | ns |
| BMR, kcal/d* | 1635 ± 142 | 1639 ± 131 | ns |
| fs-insulin, pmol/l | 94.8 ± 45.3 | 97.7 ± 63.5 | ns |
| fs-glucose, mmol/l | 5.5 ± 0.7 | 5.5 ± 0.8 | ns |
| fs-leptin, ng/l** | 32.9 ± 12.8 | 26.3 ± 4.9 | ns |
| Systolic blood pressure, mmHg | 130.7 ± 14.8 | 128.6 ± 13.2 | ns |
| Diastolic blood pressure, mm Hg | 87.4 ± 10.8 | 84.7 ± 6.6 | ns |

*Adjusted for fat free mass and age.
**The leptin levels were available from 69 subjects.

TABLE 2

Demogaphic and clinical characteristics of 64 normal weight subjects in the beginning of the follow-up study (during 1979–1981) according to the presence or absence of the Leu(7) to Pro(7) mutation in the NPY gene. The values are mean ± SD.

| Characteristic | Without mutation | With mutation |
|---|---|---|
| age, years | 55.8 ± 2.0 | 55.1 ± 1.8 |
| sex, F/M | 31/25 | 7/1 |
| BMI, kg/m² | 24.3 ± 2.0 | 24.9 ± 1.8 |
| WHR | 0.87 ± 0.08 | 0.85 ± 0.05 |
| fs-insulin, pmol/l | 74.9 ± 47.2 | 95.3 ± 23.8 |
| fs-glucose, mmol/l | 4.9 ± 0.63 | 4.5 ± 0.57 |
| Systolic blood pressure, mmHg | 142.4 ± 17.6 | 151.1 ± 16.1 |
| Diastolic blood pressure, mm Hg | 86.8 ± 9.0 | 91.1 ± 8.4 |

REFERENCES

1. Gray, T. S., Morley, J. E., Neuropeptide Y: anatomical distribution and possible function in mammalian nervous system. Nature. Feb. 3, 1986; 38(5):389–401.
2. Lundberg, J. M., Terenius, L., Hokfelt, T., Marling, C. R., Tatemoto, K., Mutt, V., Polak, J., Bloom, S., Goldstein, M. Neuropeptide Y (NPY)-like immunoreactivity in peripheral noradrenergic neurons and effects of NPY on sympathetic function. Acta Physiol Scand December 1982; 116(4):477–480.
3. Clark, J. T., Kalra, P. S., Kalra, S. P., Neuropeptide Y stimulates feeding but inhibits sexual behavior in rats. Endocrinology December 1985; 117(6):2435–2442.
4. Levine, A. S., Morley, J. E. Neuropeptide Y: a potent inducer of consummatory behavior in rats. Peptides November 1984; 5(6):1025–1029.
5. Stanley, B. G., Leibowitz, S. F. Neuropeptide Y injected in the paraventricular hypothalamus: a powerful stimulant of feeding behavior. Proc Natl Acad Sci USA June 1985; 82(11):3940–3943.
6. Heilig, M., McLeod, S., Brot, M., Heinrichs, S. C., Menzaghi, F., Koob G. F., Britton, K. T. Anxiolytic-like action of neuropeptide Y: mediation by Y1 receptors in amygdala, and dissociation from food intake effects. Neuropsychopharmacology June 1993; 8(4):357–363.

7. Wahlestedt, C., Pich, E. M., Koob, G. F., Yee, F., Heilig, M. Modulation of anxiety and neuropeptide Y-Y1 receptors by antisense oligodeoxynucleotides. Science Jan. 22, 1993; 259(5094):528–531

8. Wahlestedt, C., Skagerberg, G., Ekman, R., Heilig, M., Sundler F., Hakanson, R., Neuropeptide, Y (NPY) in the area of the hypothalamic paraventricular nucleus activates the pituitary-adrenocortical axis in the rat. Brain Res Aug. 4, 1987; 417(1):33–38

9. McDonald, J. K., Lumpkin, M. D., Samson, W. K., McCann, S. M. Neuropeptide Y affects secretion of luteinizing hormone and growth hormone in ovariectomized rats. Proc Natl Acad Sci USA January 1985; 82(2):561–564.

10. Sahu, A., Kalra, S. P., Crowley, W. R., Kalra, P. W. Testosterone raises neuropeptide-Y concentration in selected hypothalamic sites and in vitro release from the medial basal hypothalamus of castrated male rats. Endocrinology January 1989; 124(1):410–414.

11. Menendez, J. A., McGregor, I. S., Healey, P. A., Atrens, D. M., Leibowitz, S. F. Metabolic effects of neuropeptide Y injections into the paraventricularnucleus of the hypothalamus. Brain Res May 14, 1990; 516(1):8–14.

12. Moltz, J. H., McDonald J. K., Neuropeptide Y: direct and indirect action on insulin secretion in the rat. Peptides November 1985; 6(6):1155–1159.

13. Zrejevskin, Cusin I., Vettor, R., Rohner-Jeanrenaud, F., Jeanrenaud, B. Chronic intracerebroventricular NPY administration to normal rats mimics hormonal and metabolic changes of obesity. Endocrinology 133: 1753–1758.

14. Sahu, A., Sninsky, C. A., Kalra, P. S., Kalra, S. P. Neuropeptide-Y concentration in microdissected hypothalamic regions and in vitro release from the medial basal hypothalamus-preoptic area of streptozotocin-diabetic rats with and without insulin substitution therapy. Endocrinology January 1990; 126(1):192–198.

15. Stephens, T. W., Basinski, M., Bristow, P. K., Bue-Valleskey, J. M., Burgett, S. G., Craft, L., Hale, J., Hoffmann, J., Hsiung, H. M., Kriauciunas, A., et al. The role of neuropeptide Y in the antiobesity action of the obese geneproduct. Nature Oct. 12, 1995; 377(6549):530–532.

16. Schwartz, M. W., Baskin, D. G., Bukowski, T. R., Kuijper, J. L., Foster, D., Lasser, G., Prunkard, D. E., Porte, D., Jr., Woods, S. C., Seeley, R. J., Weigle, D. S. Specificity of leptin action on elevated blood glucose levels and hypothalamic neuropeptide Y gene expression in ob/ob mice. Diabetes April 1996; 45(4):531–535.

17. Pesonen, U., Huupponen, R., Rouru, J., Koulu, M. Hypothalamic neuropeptide expression after food restriction in Zucker rats: evidence of persistent neuropeptide Y gene activation. Brain Res Mol Brain Res December 1992; 16(3–4):255–260.

18. Chua, S. C., Jr., White, D. W., Wu-Peng, X. S., Liu, S. M., Okada, N., Kershaw, E. E., Chung, W. K., Power-Kehoe, L., Chua, M., Tartaglia, L. A., Leibel, R. L. Phenotype of fatty due to Gln269Pro mutation in the leptinreceptor(Lepr). Diabetes August 1996; 45(8):1141–1143.

19. Kaye, W. H., Berrettini, W., Gwirtsman, H., George, D. T. 1990 Altered cerebrospinal fluid neuropeptide Y and peptide YY immunoreactivity in anorexia and bulimia nervosa. Arch. Gen. Psychiatry 47:548–446.

20. Mordasini, R., Klose, G., Greten, H. Secondary type II hyperlipoproteinemia in patients with anorexia nervosa. Metabolism January 1978; 27(1):71–79.

21. Sanches-Muniz, F. J., Marcos, A., Varela, P. Serum lipids and apolipoprotein B values, blood pressure and pulse rate in anorexia nervosa. Eur J Clin Nutr January 1991; 45(1):33–36.

22. Uusitupa, M. I., Karhunen, L., Rissanen, A., Franssila-Kallunki, A., Niskanen, L., Kervinen, K., Kesaniemi, V. A. Apolipoprotein E phenotype modifies metabolic and hemodynamicabnormalities related to central obesity in women. Am J Clin Nutr August 1996; 64(2):131–136.

23. Sipiläinen, R., Uusitupa, M., Heikkinen, S., Rissanen, A., Laakso, M. Polymorphism of the $\beta_3$-adrenergic receptor gene affects basal metabolic rate in obese Finns. 1997. Diabetes 46: 77–80.

24. Uusitupa, M., Siitonen, O., Aro, A., Pyorala, K. Prevalence of coronary heart disease, left ventricular failure and hypertension in middle-aged, newly diagnosed type 2 (non-insulin-dependent) diabetic subjects. Diabetologia January 1985; 28(1):22–27.

25. Minth, C. D., Andrews, P. C., Dixon, J. E. Characterization, sequence, and expression of the cloned human neuropeptide Y gene. J Biol Chem Sep. 15, 1986; 261(26):11974–11979.

26. Röschlau, P., Bernt, E., Gruber, W. Enzymatische Bestimmung des Gasamtcholesterins im Serum. Z Klin Chem Biochem 1974. 12: 403–407.

27. Wahlenfield, A. W., Triglycerides. Determination after enzymatic hydrolysis. In: Bergmeyer H. U. (ed) Methods in enzymatic analysis. Academic Press. New York. pp 1831–1835.

28. Uusitupa, M., Siitonen, O., Penttila, I., Aro, A., Pyorala, K. Proteinuria in newly diagnosed type II diabetic patients. Diabetes Care March 1987; 10(2):191–194.

29. Karhunen, L., Franssila-Kallunki, A., Rissanen, A., Kervinen, K., Kesaniemi, Y. A., Uusitupa, M. Determinants of resting energy expenditure in obese non-diabetic caucasian women. Int J Obes Relat Metab Disord March 1997; 21(3):197–202.

30. Ehnholm, C., Lukka, M., Kuusi, T., Nikkila, E., Utermann, G. Apolipoprotein E polymorphism in the Finnish population: gene frequencies and relation to lipoprotein concentrations. J Lipid Res March 1986; 27(3):227–235.

31. Lundberg, J. M., Terenius, L., Hokfelt, T., Goldstein, M. High levels of neuropeptide Y in peripheral noradrenergic neurons in various mammals including man. Neurosci Lett Dec. 2, 1983; 42(2):167–172.

32. Wang, Y. N., McDonald, J. K., Wyatt, R. J. Immunocytochemical localization of neuropeptide Y-like immunoreactivity in adrenergic and non-adrenergic neurons of the rat gastrointestinal tract. Peptides January 1987; 8(1):145–151.

33. Roche, C., Boutin, P., Dina, C., Gyapay, G., Basdevant, A., Hager, J., Guy-Grand, B., Clement, K., Froguel, P. Genetic studies of neuropeptide Y and neuropeptide Y receptors Y1 and Y5 regions in morbid obesity. Diabetologia June 1997; 40(6):671–675.

We claim:

1. A DNA sequence comprising a nucleotide sequence encoding a human prepro-neuropeptide Y (preproNPY) where the leucine amino acid in position 7 of the signal peptide part of said preproNPY has been replaced by proline.

2. The DNA sequence according to claim 1 comprising the cDNA sequence set forth in SEQ ID NO:5, wherein the nucleotide T at position 106 has been replaced by the nucleotide C.

3. The DNA sequence according to claim 1 wherein said DNA sequence is cDNA.

4. An RNA sequence comprising an RNA sequence complementary to the DNA sequence of claim 1.

5. A method for screening a subject to determine if said subject is a carrier of a mutant human NPY gene, comprising the steps of providing a biological sample of the subject to be screened; and performing an assay to detect in the biological sample the presence of a i) the normal human NPY gene or ii) said mutant human NPY gene, wherein said mutant human NPY gene comprises proline at amino acid position 7 of the signal peptide in plate of the wild-type leucine.

6. A method for diagnosing a predisposition for increased serum cholesterol or LDL cholesterol level in a human subject, said method comprising determining whether said subject has a polymorphism in the signal peptide part of the human preproNPY, said polymorphism comprising the substitution of the position 7 leucine for proline in the signal peptide part of said preproNPY, said polymorphism being indicative of a predisposition to increased serum cholesterol or LDL cholesterol level.

7. A cell line expressing a mutated human NPY gene encoding a prepro-neuropeptide Y or part thereof, wherein said mutant human NPY gene comprises proline at amino acid position 7 of the signal part of said prepro-neuropeptide Y in place of the wild-type leucine and said part thereof encompasses said mutation.

* * * * *